United States Patent [19]

Shinohara et al.

[11] 4,297,192

[45] Oct. 27, 1981

[54] CATALYST SUPPORTED OXYGEN SENSOR ELEMENT AND A METHOD OF MANUFACTURING SAME

[75] Inventors: Hiroshi Shinohara, Okazaki; Yasuhiro Otsuka, Toyota; Shinichi Matsumoto, Toyota; Hiroshi Wakisaka, Toyota; Toshinobu Furutani, Toyota, all of Japan

[73] Assignee: Toyota Jidosha Kogyo Kabushiki Kaisha, Toyota, Japan

[21] Appl. No.: 104,966

[22] Filed: Dec. 18, 1979

[51] Int. Cl.³ .................... B05D 1/08; G01N 27/58
[52] U.S. Cl. ........................... 204/195 S; 427/123; 427/125; 427/126.4
[58] Field of Search .................. 204/1 S, 195 S; 427/126.4, 123, 125

[56] References Cited

U.S. PATENT DOCUMENTS

| | | | |
|---|---|---|---|
| 3,741,725 | 6/1973 | Graham | 423/213.5 |
| 3,935,089 | 1/1976 | Togana et al. | 204/195 S |
| 3,978,006 | 8/1976 | Topp et al. | 204/195 S |
| 4,021,326 | 5/1977 | Pollner et al. | 204/195 S |
| 4,119,512 | 10/1978 | Inoue et al. | 204/195 S |
| 4,177,112 | 12/1979 | Suzuki et al. | 204/1 S |

FOREIGN PATENT DOCUMENTS 2656648  6/1977  Fed. Rep. of Germany ... 204/195 S

Primary Examiner—G. L. Kaplan
Attorney, Agent, or Firm—Stevens, Davis, Miller & Mosher

[57] ABSTRACT

A catalyst supported oxygen sensor element detecting the oxygen concentration in exhaust gas from vehicle engines is composed of a tubular container of a solid ion-conductive electrolyte with the one end portion thereof closed, an inner electrode being positioned on the inner circumference of the container, an outer electrode being positioned on the outer circumference, a protective layer of a refractory material being provided on the outer circumference of the outer electrode, a catalyst layer being provided on the outer circumference of the protective layer, and optionally provided on the outer circumference of the catalyst layer, and a method of manufacturing the same.

12 Claims, 11 Drawing Figures

CATALYST SUPPORTED OXYGEN SENSOR ELEMENT AND A METHOD OF MANUFACTURING SAME

BACKGROUND OF THE INVENTION

1. Field of the Invention:

The present invention relates to an oxygen sensor element to determine oxygen concentration in exhaust gases from vehicle engines with improved sensor performance particularly in unbalanced exhaust gases where the oxygen content is excess or less.

2. Brief Description of the Prior Art:

In a system purifying exhaust gas from vehicle engines, it is of significance to determine the oxygen concentration of exhaust gases for adjusting the proper composition of the exhaust gases leading into a catalyst converter within a given range. In particular, where there is used a "three way system" which can simultaneously remove non-combusted hydrocarbons (CH), carbon monoxide (CO) and nitrogen oxides (NOx), it is necessary to adjust the exhaust gas composition within a very narrow range around the theoretical air-to-fuel ratio in order to accomplish sufficient purification of exhaust gases. For this purpose, an oxygen sensor is used to determine the oxygen concentration in exhaust gases, thereby regulating an amount of fuel to be injected into a vehicle engine in response to the determined oxygen concentration.

It is known that conventional oxygen sensors are composed generally of a container of a solid oxygen ion conductive electrolyte, such as zirconia, the inner and outer surfaces of which are provided with a metallic electrode composed of platinum or the like. The oxygen sensors of this type may measure the oxygen concentration in exhaust gases by measuring the electromotive force derived from the difference between the reference oxygen concentration produced in the container comprised of the solid electrolyte and the oxygen concentration in the exhaust gases which is brought into contact with the electrode provided on the outer surface of the container.

It is also known that such oxygen sensors are used in combination with an electronic fuel injection (EFI) apparatus or a secondary air supply apparatus, whereby the oxygen concentration in the exhaust gases in virtually balanced state can be measured. Where the oxygen concentration in balanced exhaust gas is controlled using air as the reference gas, an electromotive force of about 1 volt is produced on the exhaust gas rich side and an electromotive force of about 1/10 volt on the exhaust gas lean side. The excessive air ratio ($\lambda$) in exhaust gases can be defined by the following formula:

$$\lambda = \frac{\text{Actual Air-to-Fuel Ratio}}{\text{Theoretical Air-to-Fuel Ratio}}$$

Where the excessive air ratio ($\lambda$) is one, it means that air is reacted in approximately stoichiometric amounts with combustible substances in exhaust gases. The $\lambda$ value being more than one ($\lambda > 1$) means that the combustible substances are lean, and the $\lambda$ value being less than one ($\lambda < 1$) means that the combustible substances are rich. Where the $\lambda$ value is one in balanced exhaust gases, the electromotive force on an oxygen sensor rapidly changes from about 1 volt to about 1/10 volt so that even conventional oxygen sensors can detect whether air is supplied in proper amounts, thereby performing the regulation of the air excessive ratio.

As is well known, however, the composition of the exhaust gases from vehicle engines may deviate from a balanced state to a remarkably great extent. Unbalanced exhaust gases may be produced where an engine is operated while the $\lambda$ value is regulated below one in the air intake system and then a secondary air is injected into the exhaust system to regulate the exhaust gases at $\lambda = 1$ whereby to react with combustible substances present in the exhaust gases. In this case, the electromotive force of the oxygen sensor does not change as long as the excessive air ratio ($\lambda$) does not exceed one and is not changed to the exhaust gas lean side. In other words, an oxygen sensor may cause to change its electromotive force where exhaust gases contain air and fuel in approximately stoichiometric amounts, that is, the $\lambda$ value is one, but the electromotive force of an oxygen sensor can change in unbalanced exhaust gases only when the excessive air ratio ($\lambda$) is caused to be brought to the exhaust gas lean side. Therefore, in exhaust gases in unbalanced state, conventional oxygen sensors may not work nor measure the oxygen concentration therein with accuracy. Thus, conventional oxygen sensors are insufficient for use in unbalanced exhaust gases so that a computerized signal compensation circuit and expensive accessory circuits would be needed for the application of such conventional oxygen sensors to said exhaust gas disposal systems to provide satisfactory sensor performance.

Accordingly, many attempts have been made so far to improve characteristics of oxygen sensors, but the above-mentioned problems encountered with in the use of the conventional oxygen sensors in unbalanced exhaust gases remain unsolved.

Japanese Patent Application Laid-Open No. 137,591/1975 discloses an oxygen sensor in which a pelletized catalyst is provided on the outer surface of a conventional oxygen sensor to oxidize components of unbalanced exhaust gases. This oxygen sensor, however, is practically insufficient because the pelletized catalyst conventionally used for purification of exhaust gas are merely applied to the oxygen sensor. This oxygen sensor has not actually been applied to vehicles because the pelletized catalyst supported on an oxygen sensor element could not function effectively nor maintain its activity for a long period of time under circumstances under which the oxygen sensor is exposed to an exhaust gas system and it consecutively undergoes vibration of a vehicle, high temperature of the exhaust gases and heat impact or shocks. Further, the pelletized catalyst to be used therefor may tend to decrease its catalytic activity during operation due to the modification of the carrier from gamma-alumina to alpha-alumina. Moreover, the pelletized catalyst, when applied to an oxygen sensor element, may be subject to removal from the surface of the element owing to the continued vibration of a vehicle engine and the heat impact or shocks of the exhaust gases by the exhaust gases, and it is difficult to support the pelletized catalyst layer on the sensor element tightly enough to remain fit against the vehicle vibration and the heat shocks. Accordingly, the use of the pelletized catalyst for a sensor element leaves such problems as they are and is not practical. It is further known that there is employed for this purpose an oxygen sensor in which a refractory layer ($MgO \cdot Al_2O_3$) is provided on the outer surface of the outer electrode of the oxygen sensor element and a platinum catalyst layer is formed on the refractory layer with another layer of a refractory material formed on the outer surface of the catalyst layer. This type of the oxygen sensor element is expensive because platinum is used in plates and the catalytic efficiency of this sensor is low because the catalyst layer is placed between the two refractory layers.

It is also known that an oxygen sensor possesses a spinel catalyst layer formed on the outer surface of the outer electrode of an oxygen sensor element. This type of the oxygen sensor element cannot achieve sufficient catalytic performance because of a low availability of catalyst.

SUMMARY OF THE INVENTION

It is an object of the present invention to provide oxygen sensor element which can accurately determine the oxygen concentration of exhaust gases in unbalanced state.

Another object of the present invention is to provide an oxygen sensor element having a protective layer of refractory material provided on the outer surface of an outer electrode and having another layer of catalyst material formed on the outer surface of said protective layer.

A further object of the present invention is to provide an oxygen sensor element having further another protective layer over the outer surface of the catalyst layer.

A still further object of the present invention is to provide an oxygen sensor element having a catalyst layer formed on the outer surface of the protective layer, said catalyst layer being unlikely subject to removal from the sensor element due to vibration and heat impact.

Another principal object of the present invention is to provide a process for the manufacture of an oxygen sensor element having the structure as described hereinabove and hereinbelow.

DETAILED DESCRIPTION OF THE INVENTION

The catalyst supported oxygen sensor element in accordance with the present invention is composed of a tubular container of a solid oxygen-ion conductive electrolyte with its one end portion closed, the inner circumference of the said container being provided with an inner electrode and the outer circumference being provided with an outer electrode, the outer surface of the outer electrode being further provided with a protective layer of a refractory material, and the outer circumferential surface of the refractory protective layer being also covered with a layer of catalyst having a catalytic activity for oxidizing non-combusted substances in exhaust gases and being supported on a refractory carrier particles.

Figure 1:
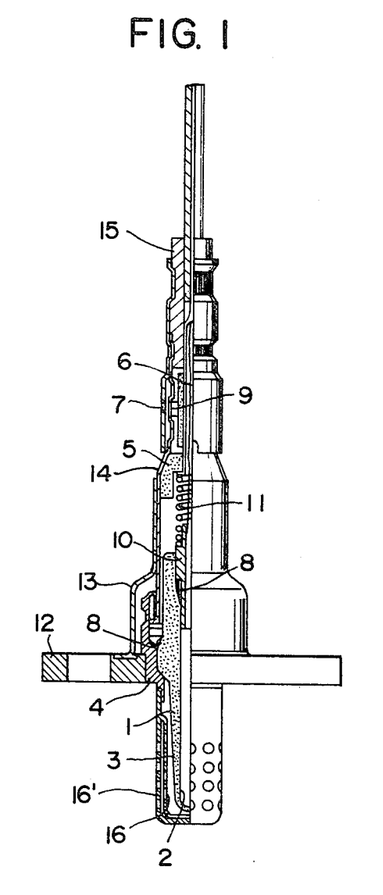
FIG. 1 is a side elevational view of an oxygen sensor provided with an oxygen sensor element in accordance with the present invention with a partially broken view to disclose construction.

Referring now to FIG. 1, there is shown an oxygen sensor in which the oxygen sensor element in accordance with the present invention is positioned. The oxygen sensor element comprises a tubular container of a solid electrolyte of zirconia, for example, with the one end portion thereof closed. The solid electrolyte container 1 is provided with an inner electrode 2 on the inner circumferential surface of the container, whereby the reference oxygen partial pressure is measured using air as the reference gas. The container is also provided with an outer electrode 3 on the outer side of the container which is arranged in such a manner as to make exhaust gas brought into contact with the surface of the outer electrode. The oxygen sensor element is then secured in appropriate manner in a housing 4 which is composed of a metal such as stainless steel unlikely to be oxidized and transformed at high temperatures. An inner louver 16 and an outer louver 16' are positioned with an appropriate space and outside the container 1 to prevent decrease in sensor performance due to a direct contact with gas flow. In FIG. 1, 5 represents an alumina insulator, 6 a lead wire, 7 an opening communicating with the outside, 8 a graphite sheet, 9 a repellent filter, 10 an output stem, 11 a spring, 12 a frange, 13 a water repellent covering, 14 a covering, and 15 a sealing material.

Figure 2:
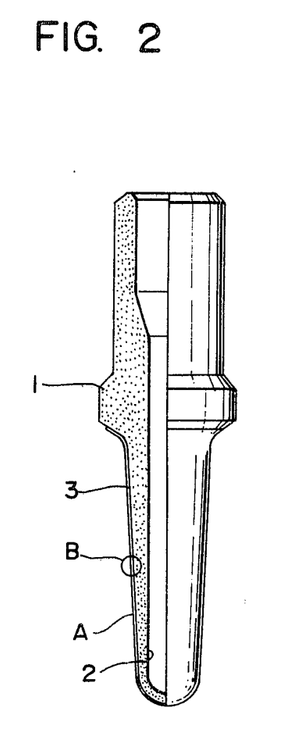
FIG. 2 is a side elevational view of an oxygen sensor element according to the present invention, with a partially broken view to disclose the construction thereof.

Referring next to FIG. 2, there is shown an example of an oxygen sensor element in accordance with the present invention. The sensor element is composed of a tubular container, with the one end portion thereof closed, of a known solid electrolyte consisting of a $ZrO_2$-$CaO$ system or a $ZrO_2$ system to which about 4-10 mole percent of $Y_2O_3$ is added. The container 1 is arranged such that air to be used as the reference gas is introduced into the container and that exhaust gases to be measured are brought into contact with the outer surface of the container. The inner circumferential surface of the container 1 is coated to from about 0.2 to about 2 microns with a porous material such as platinum which can function as the inner electrode 2. The outer circumferential surface of the container is likewise coated to from about 0.5 to about 2 microns with a porous material such as platinum. This coating can serve as the outer electrode 3. These electrodes 2, 3 consist of a portion of producing the electromotive force between the solid electrolyte and the gas, i.e., air or exhaust gases and a portion of transferring the electromotive force produced to an appropriate device, but these portions cannot be distinguished in the drawing.

Figure 3:
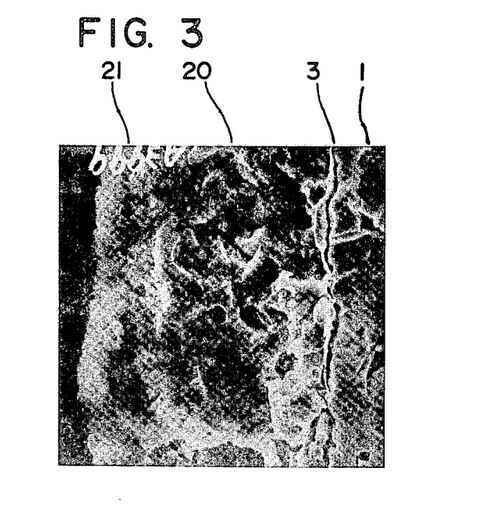
FIG. 3 is an electron microscopic photograph ($\times 100$ magnification) illustrating the state of the solid electrolyte, the outer electrode, the protective layer, and the catalyst layer formed in accordance with the present invention in the circle of B in FIG. 2.
Figure 4:
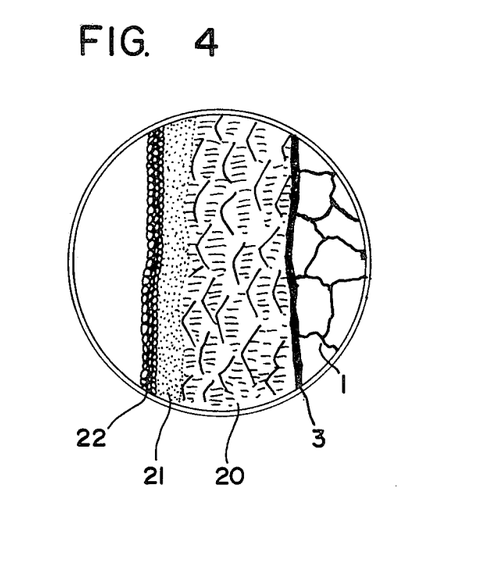
FIG. 4 is an enlarged schematical representation of the solid electrolyte, the outer electrode, the protective layer, the catalyst layer, and the additional protective layer formed in accordance with the present invention.

The solid electrolyte container is coated at its closed terminal portion to give a coating A of about 30 mm. in length from the closed end, which can serve as the outer electrode 3. It is noted, however, that the length of a coating may be varied depending upon the size of a sensor element and so forth. FIGS. 3 and 4 illustrate the composite structures of the coating A in which 1 is the schematic representation of the structure of the solid electrolyte, 3 the porous coating layer serving as the outer electrode, 20 a protective layer of a refractory material, 21 a catalyst layer, and 22 an outer protective coating layer (in FIG. 4). FIG. 3 shows the basic structure of the coating A in accordance with the present invention. The catalyst layer 21 formed on the outer surface of the protective layer 20 may be a multilayer structure. For example, the catalyst layer may be a two-layer structure in which one layer is composed of a catalyst supported in a greater amount on a carrier and the other is composed of the same catalyst supported in a less amount on the same carrier or in which one is composed of a catalyst supported on a carrier and the other is composed of a different catalyst supported on the same or different carrier.

The electrodes to be provided on the inner and outer surfaces of the electrolyte container are usually composed of a platinum metal. The platinum electrode provided on the outer surface of the container is formed in a manner such that the layer may possess a number of small pores into which the exhaust gases to be measured can penetrate. The thickness of the coating is not limited to a particular one, but a thickness ranging from less than about 2 microns.

The protective layer to be formed on the outer electrode can serve as protecting the outer electrode from the physical and chemical corrosion by high temperature exhaust gases and allowing the electrode to adhere tightly to the solid electrolyte container. A material to be used for this purpose is refractory in nature and porous and may be an oxide such as $MgO.Al_2O_3$ (spinel type), $Al_2O_3$, $CaO.ZrO_2$ and $Y_2O_3.ZrO_2$. It is preferred to use the same material for the protective layer as that for the solid electrolyte because of no differencial thermal expansion coefficient. In order to have the exhaust gases penetrate through the pores of the protective layer to the electrode in as short a time as possible and attain the effect of joining the electrode tightly to the container, the pores of the protective layer may range from about 0.02 to about 0.5 microns in diameter and from about 30 to about 110 microns, preferably from about 50 to about 110 microns, and more preferably from about 70 to about 90 microns in thickness. The protective layer may be prepared in conventional manner, for example, by flame spraying the desired material onto the electrode, thereby providing a coating with certainty and with good coating performance.

The catalyst layer to be formed on the protective layer may contain at least one of platinum, rhodium and palladium or a mixture thereof, platinum being the most preferred and a mixture of platinum with the other being preferred. The catalytic metal may be used in an amount of from about 0.3 to about 30 percent by weight, preferably more than about 1 percent by weight, and more particularly more than about 3 percent by weight of the total weight of the catalyst material. The catalytic metal may be contained in an amount from about 5 to about 40 mg per an oxygen sensor element. When rhodium and/or palladium is used preferably in admixture with platinum, the weight of the rhodium and/or palladium with respect to the weight of the platinum may be to the extent of about 50 percent. The finely divided carrier particles to which the catalytic metal is allowed to adhere may be from about 1 to about 10 microns in diameter.

The catalyst component or components to be contained in the catalyst layer formed on the outer circumference of the protective layer in accordance with the present invention may be prepared in conventional manner, for example, by immersing into a chloroplatinic acid solution having a predetermined platinum content an appropriate amount of finely divided gamma-$Al_2O_3$ particles of preferably from about 1 to about 10 microns in particle diameter, drying the immersed alumina particles, burning the dried particles, mixing the burned particles with a binder such as alumina sol or aluminum nitrate, and ball milling the mixture to a sufficient extent to give a slurry.

The catalyst layer may be formed in conventional manner, for example, by coating an aqueous slurry, as prepared above, containing the finely divided alumina particles on which the catalyst component or components are supported, drying the element having the immersed coating at room temperature, and burning the dried element at 400°–600° C. The catalyst layer may also be formed in conventional manner, for example, by immersing the sensor element having the protective layer in an aqueous slurry containing finely divided alumina particles and a binder such as alumina sol or aluminum nitrate or spraying the aqueous slurry over the element to an appropriate depth to form a coating, drying the coated element, burning the dried element, and then immersing the burnt element into a solution or slurry containing the catalyst component or components or spraying such a solution or slurry over the surface of the burnt coating serving as a carrier coating. The element of a catalyst coating is then dried and burned as above. The burning of the coated element can make the adherence intensity between the protective and catalyst layers.

As the thickness of the catalyst layer may affect a time of response to a change in the oxygen concentration in exhaust gas and a catalytic activity, the thickness of the catalyst layer may preferably range from about 5 to about 50 microns. The thickness of the catalyst layer, however, may be varied depending upon the kind of a carrier and/or a catalyst component or components or the like.

The catalyst layer to be formed may be in the length of about $\frac{1}{2}$ to about $\frac{1}{3}$ of the total length of the protective layer from the closed end of the sensor element as the terminal portion thereof can function as a sensing portion more than the other portion thereof. It is, however, possible to form a catalyst layer over the whole length of the protective layer formed on the outer electrode, but it is not practically necessary to do so from the economic point of view.

The catalyst layer prepared as above is secured tightly to the surface of the protective layer so that the catalyst layer is hardly removed from the sensor element upon vibration of a vehicle and heat influences of exhaust gas. The catalyst component or components to be supported on the catalyst layer prepared as above can maintain the catalytic activity for a long period of time because of little mechanical actions being undergone. The catalyst layer so formed can oxidize some exhaust gas components in exhaust gas in unbalanced state, whereby the sensor temperature can be elevated. The sensor temperature may often be lower than that of the ambient exhaust gas by about 100° C. while the temperature of the exhaust gas is about 450°–500° C., whereby the oxygen sensor cannot work accurately. The catalyst layer formed on the protective layer can also accelerate the reach of the oxygen atoms because combustible exhaust gas components other than oxygen atom, which may reach the outer electrode faster than the oxygen atom are oxidized, and make the change in the electromotive force in an oxygen sensor element around $\lambda = 1$. Although conventional oxygen sensors may often give a false signal as "more oxygen" while the oxygen atoms are still present in an ample amount in a system because it is assumed that the combustible substances other than oxygen atom reach the outer electrode before the reach thereto of the oxygen atom, the oxygen sensor provided with the sensor element having the structure as above in accordance with the present invention can function with accuracy even in exhaust gas in unbalanced state. The term "unbalanced" in the words "unbalanced exhaust gas" and "unbalanced state" used hereinabove and hereinbelow means that the excessive air ratio deviates substantially from the $\lambda$ value being one. The term "balanced" means that the excessive air ratio ($\lambda$) is substantially around the $\lambda$ value being one.

An additional protective layer may be optionally provided on the outer circumference of the catalyst layer. The protective layer may be formed in the same manner and mode as the protective layer formed immediately on the outer surface of the outer electrode.

The following examples will illustrate the present invention more in detail, but should be construed as not limiting the present invention thereto in any sense and manner.

EXAMPLE

A tubular container, with the one end portion thereof closed, was provided at the outer and inner circumferences thereof with a platinum electrode to each of which a lead wire is connected, thereby enabling the measurement of the electromotive forces developed in the inner and outer electrodes.

The outer surface of the outer electrode of the sensor element was coated by flame spraying $MgO.Al_2O_3$ (spinel) as a refractory material to a given thickness to provide a protective layer.

The protective layer was further coated with an aqueous slurry containing platinum supported on gamma-alumina ($\gamma$-$Al_2O_3$) particles having a particle size ranging from about 1 to 10 microns and an average particle diameter of 2.2 microns and aluminum nitrate as a binder. The amount of the platinum in the protective layer was about 3 percent by weight. The coated sensor element was dried and burned. The resulting element has a sensing area of 7.00 cm.$^2$ (the length of 30 mm. from the end of the sensor element). The sensor element prepared hereinabove was tested for its sensor performances as follows:

EXPERIMENTAL EXAMPLE 1

Figure 5:
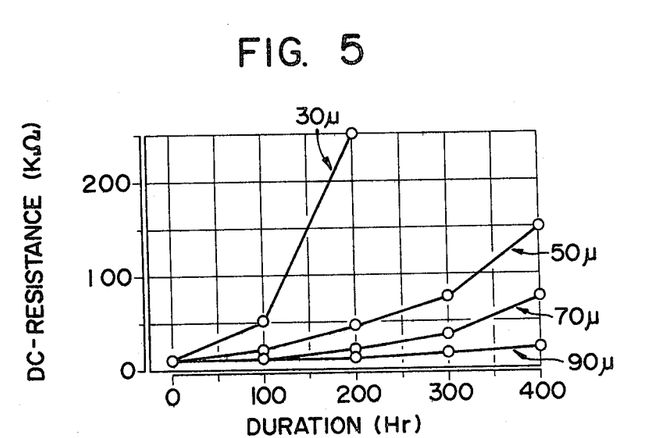
FIG. 5 is a graph illustrating the relationship of the direct current resistance (DC-R) of the oxygen sensor element with a period of duration.

The oxygen sensor element prepared hereinabove was tested for its duration. The test results will be shown in FIG. 5, in which the ordinate represents a direct current resistance of the sensor element and the abscissa represents a period of duration. The numericals represented in FIG. 5 mean the thickness of the protective layer of the test sensor element. From FIG. 5, it will be noted that the direct current resistance for the test element having the thickness of 30 microns is too large and the test elements having the thickness of more than 50 microns give a good result.

The period of duration was determined by operating an engine at a revolution for 2 hours during which exhaust gas having a temperature of 800° C. was generated and then for another 1 hours during which exhaust gas having a temperature of 400° C. and repeating these operations alternately in this order.

EXPERIMENTAL EXAMPLE 2

Figure 6:
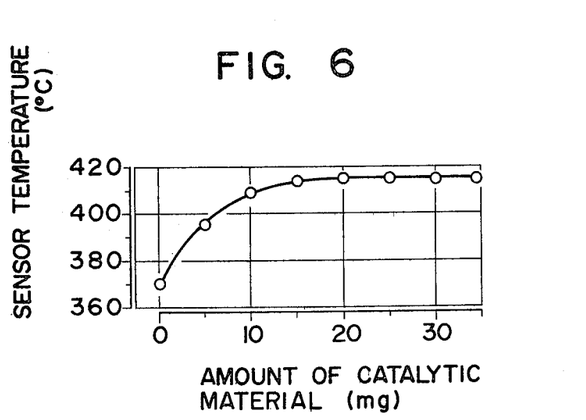
FIG. 6 is a graph illustrating the relationship of an amount of catalyst of the oxygen sensor element with a sensor temperature.

The sensor elements having a protective layer of 70 microns in thickness were prepared in which the amounts of catalysts (platinum-to-rhodium=9:1) were varied as shown in FIG. 6, in the same manner as Example above. Unless otherwise noted, sensor elements to be used for subsequent tests were also prepared in the same manner as Example above.

FIG. 6 shows the relationship of the amount of catalyst contained in the catalyst layer with the oxygen sensor element terminal temperature was observed. In this test results, it is noted that, where no catalyst is contained, the sensor element terminal temperature was about 370° C. while the terminal temperature of the test sensor element having a catalyst layer containing more than 15 mg. of platinum was about 415° C. It is evident therefrom that the use of the catalyst increased the terminal temperature by about 50° C.

The test was carried out by means of a testing machine by measuring the terminal temperature of the test element on a thermocouple attached to the inner wall of the sensor element terminal.

EXPERIMENTAL EXAMPLE 3

Figure 7:
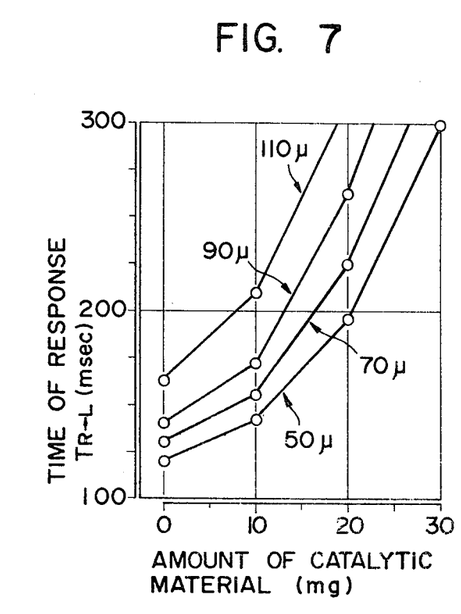
FIG. 7 is a graph illustrating the relationship of an amount of catalyst with a time of response ($T_{R \rightarrow L}$)

The sensor elements was prepared in which the amounts of catalyst contained in the catalyst layer having the platinum to rhodium ratio of 9:1 and having an amount of 3 percent by weight of the catalyst metals were varied and the thicknesses of the protective layers were varied as shown in FIG. 7.

The sensor elements prepared above were tested for a time of response necessary to reach the determined electromotive force of the sensor element output when a situation where exhaust gases were rich ($\lambda = 0.6$) was changed rapidly to a situation where exhaust gases were lean ($\lambda = 3.0$), using test exhaust gases.

FIG. 7 shows that the more the amount of the coated catalyst and the thicker the protective layer, the longer the response time is.

EXPERIMENTAL EXAMPLE 4

The sensor elements having a protective layer of 50 microns in thickness were prepared in the same manner as in Experimental Example 3, in which the average particle size of the catalyst having the platinum to rhodium of 9:1 was varied. The average particle size of the catalyst is a $D_{50}$ average particle size.

Figure 8:
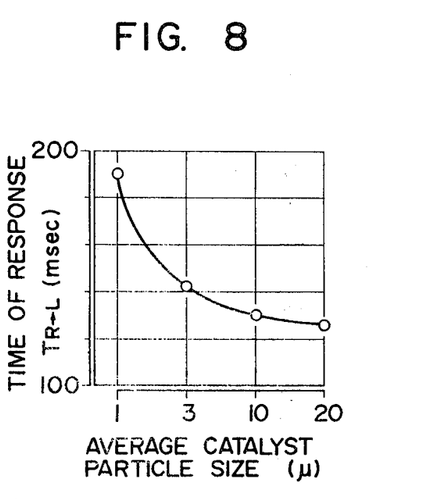
FIG. 8 is a graph illustrating the relationship between a particle size of catalyst and a time of response.

FIG. 8 shows the relationship of the amounts of the catalyst with the time of response. As shown in FIG. 8, a larger average particle size of the catalyst may give a shorter time of response.

EXPERIMENTAL EXAMPLE 5

The sensor elements having a protective layer of 70 microns in thickness were prepared in which the platinum-to-rhodium ratio in the catalyst layer containing the catalyst in an amount of 3 percent by weight was varied.

Figure 9:
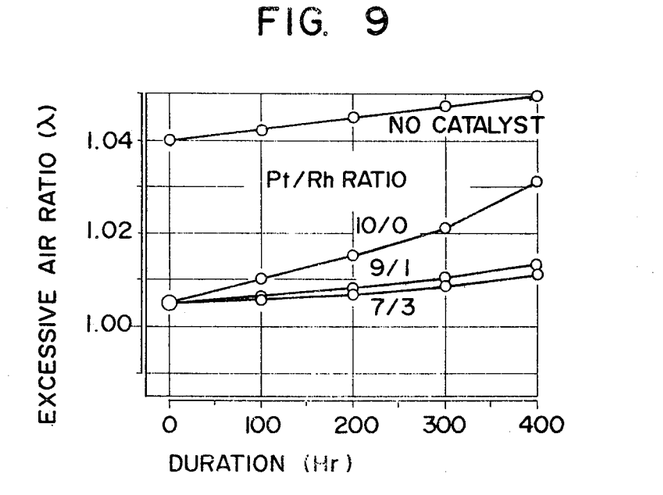
FIG. 9 is a graph illustrating of an excessive air ratio ($\lambda$) of the exhaust gases at the time of the feedback control with a period of duration.

FIG. 9 shows the relationship of the period of duration with the excessive air ratio (λ) capable of being regulated by an oxygen sensor element. It is clear from the test results that the λ value of the element containing no catalyst is remarkably higher than those of the sensor elements containing the catalyst in accordance with the present invention. It will be noted that the λ value is increased with the period of duration because of the deterioration of the catalyst layer or the catalyst poisoning action of various components contained mainly in lubricants, etc.

EXPERIMENTAL EXAMPLE 6

Figure 10:
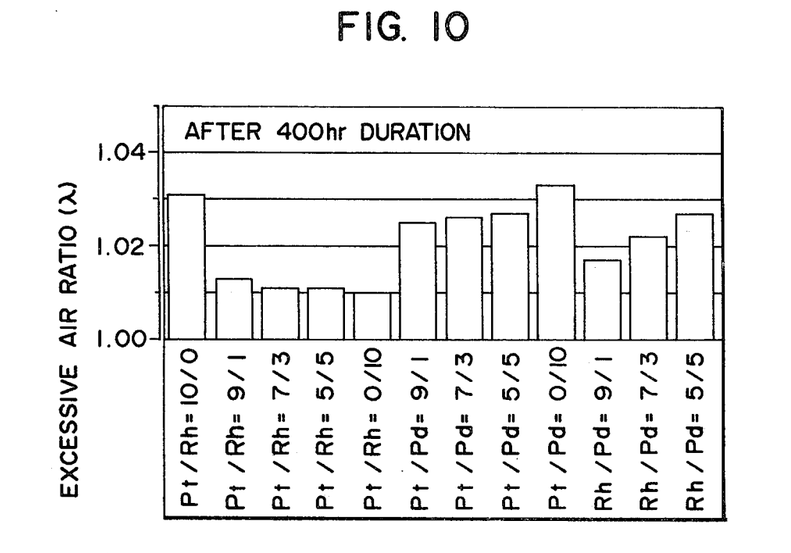
FIG. 10 is a graph illustrating the relationship of a mixture ratio of catalyst metals with an excessive air ratio ($\lambda$), as mentioned above.

The sensor elements having a protective layer of 70 microns in thickness and a catalyst layer containing the catalyst in an amount of 3 percent by weight and 10 mg. of the catalyst supported on the carrier were prepared in which the catalysts and the ratio of the catalysts to be used were varied. The excessive air ratio (λ) was determined after duration tested for 400 hours. The results are shown in FIG. 10.

EXPERIMENTAL EXAMPLE 7

The sensor elements having a protective layer of 70 microns in thickness and a catalyst layer having the platinum-to-rhodium of 9:1 were prepared in which the amounts of the catalyst were varied.

Figure 11:
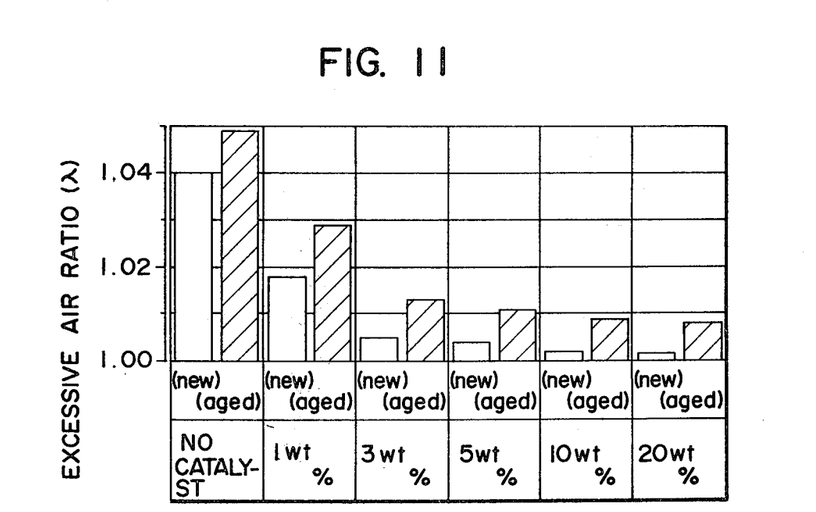
FIG. 11 is a graph illustrating the relationship of an amount of catalyst with respect to the carrier with an air excessive ratio ($\lambda$) as mentioned above.

FIG. 11 shows the relationship of the excessive air ratio (λ) with the amounts of the catalyst. In FIG. 11, the term "new" means before the duration test and the term "aged" means after the duration test for 400 hours.

What is claimed is:

1. In an oxygen sensor element detecting the oxygen concentration in exhaust gas from vehicle engines comprising a tubular container of a solid electrolyte conductive of ions with one end portion closed, an inner electrode positioned on the inner circumference of the tubular container and an outer electrode positioned on the outer circumference thereof, the improvement which comprises a protective layer of $MgO.Al_2O_3$ formed on the outer circumference of the outer electrode and a catalyst layer formed on the outer circumference of the protective layer, said catalyst layer comprising an alumina carrier and one or more oxidation catalysts.

2. The oxygen sensor element of claim 1, wherein the catalyst carrier comprises gamma-alumina.

3. The oxygen sensor element of claim 1, wherein the oxidation catalyst supported on the catalyst carrier is platinum, palladium or rhodium or a mixture thereof.

4. An oxygen sensor element of claim 1, wherein the amount of the catalyst components in the catalyst layer is from about 0.3 to about 30 percent by weight of the total weight of the catalyst layer.

5. An oxygen sensor element of claim 1, wherein the amount of the catalyst to be coated is from about 5 to about 40 mg. per oxygen sensor element.

6. An oxygen sensor element of claim 1, wherein the thickness of the catalyst layer is from about 5 to about 50 microns.

7. The oxygen sensor element of claim 1, wherein the particle size of gamma-alumina is 20 microns or smaller.

8. The oxygen sensor element of claim 1, wherein the catalyst layer covers more than substantially one-third the total length of the protective layer from the tip end thereof.

9. A method of manufacturing an oxygen sensor element which comprises the steps of; forming an inner electrode on the inner circumference of a tubular container of a solid electrolyte conductive of ion with one terminal portion closed and an outer electrode on the outer circumference thereof; forming a protective layer of $MgO.Al_2O_3$ on the outer circumference of the outer electrode by flame spraying; and thereafter forming a catalyst layer on the outer circumference of the protective layer by applying an aqueous slurry comprising an alumina carrier, an oxidation catalyst and binder, followed by drying and burning.

10. A method of manufacturing an oxygen sensor element which comprises the steps of; forming an inner electrode on the inner circumference of a tubular container of a solid electrolyte conductive of ion with one terminal portion closed and an outer electrode on the outer circumference thereof; forming a protective layer of $MgO.Al_2O_3$ on the outer circumference of the outer electrode by flame spraying; applying an aqueous slurry containing alumina particles and binder onto the protective layer-formed tubular container; immersing said tubular container into a solution or slurry containing one or more catalyst components after drying and burning, followed by drying and burning so as to form a catalyst layer.

11. The method of manufacturing an oxygen sensor element of claim 10 wherein a solution or slurry containing alumina particles and binder is applied onto said protective layer-formed tubular container by spraying.

12. A method of manufacturing an oxygen sensor element of claim 10 wherein a solution or slurry containing alumina particles and binder is applied to said protective layer-formed tubular container by immersion.

* * * * *